United States Patent
Nöcker et al.

(10) Patent No.: US 12,390,403 B2
(45) Date of Patent: *Aug. 19, 2025

(54) AQUEOUS OXIDATIVE COMPOSITION COMPRISING ORTHODIPHENOLS OR IMIDAZOLIDIN-2,4-DIONE DERIVATIVES

(71) Applicant: KAO CORPORATION, Tokyo (JP)

(72) Inventors: Bernd Nöcker, Darmstadt (DE); Qi Uellner, Darmstadt (DE); Steven Breakspear, Darmstadt (DE)

(73) Assignee: KAO CORPORATION, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 18/555,750

(22) PCT Filed: Apr. 26, 2022

(86) PCT No.: PCT/EP2022/061007
§ 371 (c)(1),
(2) Date: Oct. 17, 2023

(87) PCT Pub. No.: WO2022/229158
PCT Pub. Date: Nov. 3, 2022

(65) Prior Publication Data
US 2024/0207150 A1   Jun. 27, 2024

(30) Foreign Application Priority Data
Apr. 26, 2021 (EP) .................................. 21170399

(51) Int. Cl.
| A61Q 5/10 | (2006.01) |
| A61K 8/22 | (2006.01) |
| A61Q 5/04 | (2006.01) |
| A61Q 5/08 | (2006.01) |

(52) U.S. Cl.
CPC .............. *A61K 8/22* (2013.01); *A61Q 5/04* (2013.01); *A61Q 5/08* (2013.01); *A61K 2800/4322* (2013.01); *A61K 2800/52* (2013.01); *A61K 2800/596* (2013.01); *A61K 2800/88* (2013.01)

(58) Field of Classification Search
CPC .............. A61K 8/22; A61K 2800/4322; A61K 2800/52; A61K 2800/596; A61K 2800/88; A61K 8/463; A61K 8/347; A61K 8/4946; A61Q 5/04; A61Q 5/08; A61Q 5/10
USPC .......................................................... 8/405
See application file for complete search history.

(56) References Cited

U.S. PATENT DOCUMENTS

| 4,668,236 | A | * | 5/1987 | Grollier | A61K 8/418 |
| | | | | | 8/405 |
| 4,931,066 | A | * | 6/1990 | Grollier | A61K 8/418 |
| | | | | | 8/408 |
| 7,189,267 | B2 | * | 3/2007 | Dreher | A61K 8/90 |
| | | | | | 424/70.2 |
| 2017/0326048 | A1 | * | 11/2017 | Wahler | A61K 8/19 |
| 2017/0354584 | A1 | | 12/2017 | Lalleman et al. | |

FOREIGN PATENT DOCUMENTS

| EP | 3 229 757 A1 | 10/2017 | |
| JP | 2010195770 A | * 9/2010 | ............... A61Q 5/10 |
| WO | WO 2016/091817 A1 | 6/2016 | |
| WO | WO 2016/097246 A1 | 6/2016 | |

OTHER PUBLICATIONS

STIC Search Report dated Nov. 12, 2024.*
International Search Report & Written Opinion mailed on Jan. 27, 2021 in PCT/EP2022/061007 filed on Sep. 8, 2022 (8 pages).
(Continued)

*Primary Examiner* — Eisa B Elhilo
(74) *Attorney, Agent, or Firm* — Oblon, McClelland, Maier & Neustadt, L.L.P.

(57) ABSTRACT

A composition having a pH in a range of 1 to 6, containing hydrogen peroxide, and one or more compounds selected from orthodiphenols, imidazolidin-2,4-diones, and salts thereof. The orthodiphenols have the following general structure:

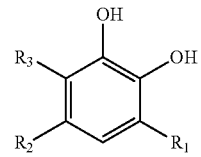

where $R_1$, $R_2$, and $R_3$ are independently selected from H, OH, halogen, $C_1$-$C_{12}$ linear or branched alkyl or alkenyl, O—X, $NO_2$, COOH, $SO_3H$, aryl, and heteroaryl, and X is a $C_1$-$C_{12}$ linear or branched alkyl. The imidazolidin-2,4-diones have the following general structure:

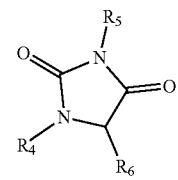

where $R_4$, $R_5$, and $R_6$ are independently selected from H, OH, halogen, $C_1$-$C_{12}$ linear or branched alkyl or alkenyl, O—X, COOH, phenyl, diphenyl, ureyl, and X is a $C_1$-$C_{12}$ linear or branched alkyl.

19 Claims, No Drawings

(56) References Cited

OTHER PUBLICATIONS

European Search Report dated Nov. 22, 2021 in EP Application 21170399.6 filed on Apr. 26, 2021 (7 pages.

* cited by examiner

AQUEOUS OXIDATIVE COMPOSITION COMPRISING ORTHODIPHENOLS OR IMIDAZOLIDIN-2,4-DIONE DERIVATIVES

CROSS REFERENCE TO RELATED APPLICATIONS

This application is a National Stage entry under 35 U.S.C. § 371 of PCT/EP2022/061007, filed on Apr. 26, 2022, and claims priority to European Patent Application No. 21170399.6, filed on Apr. 26, 2021. The entire contents of both are incorporated herein by reference.

FIELD OF THE INVENTION

The present invention relates to an aqueous oxidative composition comprising orthodiphenols or imidazolidin-2,4-dione derivatives. Furthermore, oxidative dyeing, bleaching, and perming processes using the composition are disclosed.

BACKGROUND OF THE INVENTION

Aqueous, hydrogen peroxide-containing compositions are well known in the art. These compositions are essential components in many industrial and artisanal processes. For example, bleaching or dyeing of solid substrates require the presence of oxidizing compositions. In particular paper, wool, and cosmetic industry rely on the performance of these compositions.

However, a common problem of such compositions is that the hydrogen peroxide tends to undergo a decomposition process during storage whereby the available active oxygen in the composition decreases over time. This decomposition process particularly represents a problem for bleaching, dyeing, and permanent waving processes. It is essential for the user of hydrogen-peroxide compositions that they have a long shelf life in order to retain their original performance.

The self-decomposition process of hydrogen peroxide increases with temperature. Thus, decomposition progresses faster in warm climate countries or under less than ideal storage conditions at the user's facilities. As a result, the user is confronted with lower performance in coloring, bleaching, or permanent waving processes compared to results obtained a couple of months ago with compositions having shorter storage times.

The prior art has not sufficiently solved this problem.

SUMMARY OF THE INVENTION

The first object of the present invention is an aqueous oxidizing composition A having a pH in the range of 1 to 6 comprising:
  a) hydrogen peroxide, and
  b) one or more compound(s) selected from:
  1) one or more orthodiphenol(s) and/or their derivatives, and/or their mixtures, and/or their salt(s),
  2) one or more imidazolidin-2,4-dione(s) and/or their derivatives, and/or their mixtures, and/or their salt(s).

The second object of the present invention is a kit-of-parts comprising composition A as defined above and one more composition selected from:
  a bleaching composition B comprising one or more persalt(s) and/or peroxy salt(s) and one or more alkalizing agent(s),
  an aqueous lightening composition C comprising one or more alkalizing agent(s) and having a pH in the range of 7 to 12,
  an aqueous dyeing composition D having a pH in the range of 7 to 12 and comprising one or more dye selected from oxidative dye precursor(s), oxidative dye coupler(s), and/or direct dye(s), and/or their salt(s), and/or their mixtures.
  an aqueous permanent waving composition E having a pH in the range of 3 to 12 comprising one or more reducing agent(s) and one or more alkalizing agent(s).

The third object of the present invention is a method for bleaching and/or lightening of keratin fibers, preferably human keratin fibers, more preferably human hair comprising the steps of:
  i) providing composition A as defined above,
  ii) mixing composition A with a bleaching composition B or an aqueous lightening composition C as defined above to prepare a ready-to-use composition having a pH in the range of 7 to 12,
  iii) applying the ready-to-use composition onto keratin fibers and leaving it for a time period in the range of 1 to 60 min,
  iv) rinsing off the keratin fibers and optionally shampooing the keratin fibers.

The fourth object of the present invention is a method for dyeing of keratin fibers, preferably human keratin fibers, more preferably human hair, comprising the steps of:
  xi) providing composition A as defined above,
  xii) mixing composition A with a dyeing composition D as defined above to prepare a ready-to-use composition having a pH in the range of 7 to 12,
  xiii) applying the ready-to-use composition onto keratin fibers and leaving it for a time period of 1 to 60 min,
  xiv) rinsing off the keratin fibers and optionally shampooing the keratin fibers.

The fifth object of the present invention is a method for permanently shaping keratin fibers, preferably human keratin fibers, more preferably human hair, comprising the steps of:
  xxi) optionally shampooing the keratin fibers,
  xxii) putting keratin fibers under mechanical tension,
  xxiii) applying to keratin fibers an aqueous permanent waving composition E as defined above, and leaving the composition for a time period in the range of 1 min to 60 min,
  xxiv) optionally rinsing off the composition,
  xxv) providing composition A as defined above, applying it to keratin fibers and leaving it for a time period in the range of 1 min to 30 min,
  xxvi) releasing mechanical tension from keratin fibers,
  xxvii) rinsing off the keratin fibers and optionally shampooing the keratin fibers, with the provision that steps xxii) and xxiii) as well as steps xxvi) and xxvii) may be performed in any order.

The sixth object of the present invention is a use of one or more compound(s) selected from
  1) one or more orthodiphenol(s) and/or their derivatives, and/or their mixtures, and/or their salt(s),
  2) one or more imidazolidin-2,4-dione(s) and/or their derivatives, and/or their mixtures, and/or their salt(s), for improving storage stability of aqueous compositions comprising hydrogen peroxide.

DETAILED DESCRIPTION OF THE INVENTION

Despite the attempts of the prior art, no satisfactory solution could be delivered to improve chemical and physical storage stability of aqueous oxidizing compositions comprising hydrogen peroxide.

Inventors of the present invention have unexpectedly found out that compounds of groups b1) and b2) of claim 1 increase chemical and physical storage stability of aqueous oxidizing compositions comprising hydrogen peroxide at room and elevated temperature alike. Thus, bleaching/lightening, oxidative dyeing, and permanent waving processes were unexpectedly found to be more consistent in performance over time.

Aqueous Oxidizing Composition

The present invention is directed to an aqueous oxidizing composition A having a pH in the range of 1 to 6 comprising:
a) hydrogen peroxide, and
b) one or more compound(s) selected from:
 1) one or more orthodiphenol(s) and/or their derivatives, and/or their mixtures, and/or their salt(s),
 2) one or more imidazolidin-2,4-dione(s) and/or their derivatives, and/or their mixtures, and/or their salt(s).

It is preferred from the viewpoint of storage stability and safety of the composition that the pH of the composition is 1.25 or more, more preferably 1.5 or more, further more preferably 2 or more.

It is preferred from the viewpoint of storage stability of the composition that the pH of the composition is 5 or less, more preferably 4 or less, further more preferably 3 or less.

For attaining the above-mentioned effects, it is preferred that the pH of the composition is in the range of 1.25 to 5, more preferably in the range of 1.5 to 4, further more preferably in the range of 2 to 3.

It is further preferred from the viewpoint of product performance that the concentration of the compound according to a) is 0.1% by weight or more, more preferably 0.5% by weight or more, further more preferably 1% by weight or more, still further more preferably 3% by weight or more, calculated to the total weight of the composition.

It is further preferred from the viewpoint of product performance and user safety that the concentration of the compound according to a) is 20% by weight or less, more preferably 15% by weight or less, further more preferably 12% by weight or less, calculated to the total weight of the composition.

For attaining the above-mentioned effects, it is preferred that the concentration of the compound according to a) is in the range of 0.1% to 20% by weight, preferably in the range of 0.5% to 15% by weight, more preferably in the range of 1% to 12% by weight, further more preferably in the range of 3% to 12% by weight, calculated to the total weight of the composition.

It is preferred from the viewpoint of commercial availability that one or more compound(s) according to group b1) is selected from
Flavonols,
Anthocyanidines,
Anthocyanines or anthocyanes,
Orthohydroxybenzoates,
Flavones,
Hydroxystilbenes,
3,4-dihydroxyphenylalanine and its derivatives,
2,3-dihydroxyphenylalanine and its derivatives,
4,5-dihydroxyphenylalanine and its derivatives,
Dihydroxycinnamates,
Orthopolyhydroxycoumarines,
Orthopolyhydroxyisocoumarines,
Orthopolyhydroxycoumarones,
Orthopolyhydroxyisocoumarones,
Orhtopolyhydroxychalcones,
Orhtopolyhydroxychromones,
Orhtopolyhydroxyquinones,
Orhtohydroxyxanthones,
1,2-dihyroxybenzenes and its derivatives,
1,2,4-trihydroxybenzenes and its derivatives,
1,2,3-trihydroxybenzenes and its derivatives,
2,4,5-trihydroxybenzenes and its derivatives,
Proanthocyanidines,
Proanthocyanines,
Tannic acid,
Ellagic acid,
one or more compound(s) according to the following general structure:

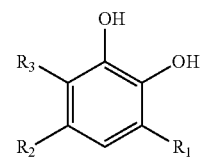

wherein $R_1$, $R_2$, and $R_3$ are independently selected from H, OH, halogen, $C_1$-$C_{12}$ linear or branched alkyl or alkenyl, O—X, $NO_2$, COOH, $SO_3H$, aryl, heteroaryl, and/or their salt(s), and/or their mixtures, with X being $C_1$-$C_{12}$ linear or branched alkyl.
and/or their salt(s), and/or their mixture(s).

It is preferred from the viewpoint of stabilization that one or more compound(s) according to group b1) is selected from the following general structure:

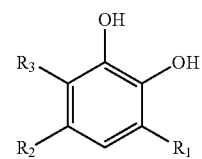

wherein $R_1$, $R_2$, and $R_3$ are independently selected from H, OH, halogen, $C_1$-$C_{12}$ linear or branched alkyl or alkenyl, O—X, $NO_2$, COOH, $SO_3H$, aryl, heteroaryl, and/or their salt(s), and/or their mixtures, with X being $C_1$-$C_{12}$ linear or branched alkyl.

It is preferred from the viewpoint of stabilization that for group b1) $R_1$ is selected from H, OH, halogen, $C_1$-$C_{12}$ linear or branched alkyl or alkenyl, O—X, $NO_2$, COOH, $SO_3H$, aryl, heteroaryl, with X being $C_1$-$C_{12}$ linear or branched alkyl, and $R_2$, and $R_3$ are independently selected from $C_1$-$C_{12}$ linear or branched alkyl or alkenyl, O—X, $NO_2$, COOH, $SO_3H$, and/or their salt(s), and/or their mixtures, with X being $C_1$-$C_{12}$ linear or branched alkyl.

It is preferred from the viewpoint of commercial availability that at least one compound according to group b1) is selected from:

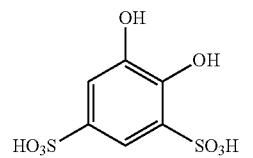

1,4-dihydroxy-1,3-benzenedisulfonic acid (tiron)

-continued

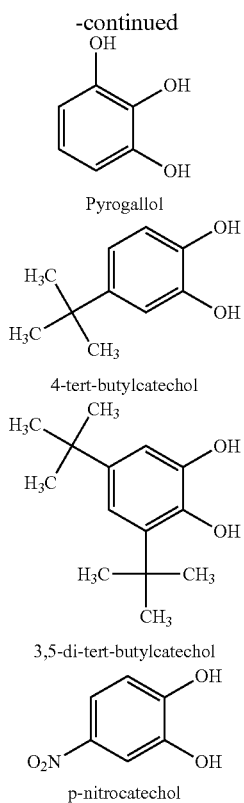

Pyrogallol 4-tert-butylcatechol 3,5-di-tert-butylcatechol p-nitrocatechol and/or their salt(s), and/or their mixtures, more preferably one or more compound according to group b1) is tiron and/or its salt(s).

The most preferred compound of group 1) from the viewpoint of stabilization is tiron and/or its salt(s).

It is preferred from the viewpoint of commercial availability that one or more compound(s) according to group b2) is according to the following general structure:

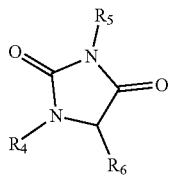

wherein $R_4$, $R_5$, and $R_6$ are independently selected from H, OH, halogen, $C_1$-$C_{12}$ linear or branched alkyl or alkenyl, O—X, COOH, phenyl, diphenyl, ureyl, and/or their salt(s), and/or their mixtures, with X being $C_1$-$C_{12}$ linear or branched alkyl.

Suitably, one or more compound(s) according to group b2) is:
hydantoin,
dichlordimethylhydantoin,
bromchlordimethylhydantoin,
dibromdimethylhydantoin,
ethotoin,
phenytoin,
mephenytoin,
fosphenytoin,
allantoin,
and/or their salt(s), and/or their mixtures.

The most preferred compound(s) of group b2) from the viewpoint of commercial availability is/are hydantoin and/or allantoin, and/or its/their salt(s), and/or their mixtures, most preferably it is hydantoin and/or its salt(s).

The artisan will recognize that mixtures of compound(s) according to groups b1) and b2) may be employed as well.

Thus, the disclosure of the present invention also is directed to an aqueous oxidizing composition A having a pH in the range of 1 to 6 comprising:
a) hydrogen peroxide, and
b) one or more compound(s) selected from:
1) tiron and/or its salt(s),
2) hydantoin, and/or their salt(s), and/or their mixtures.

It is further preferred from the viewpoint of stabilizing performance that the total concentration of compounds according to b) is 0.001% by weight or more, more preferably 0.005% by weight or more, further more preferably 0.01% by weight or more, still more preferably 0.03% by weight or more, calculated to the total weight of the composition.

It is further preferred from the viewpoint of economic reasons as well as stabilizing performance that the total concentration of compounds according to b) is 0.5% by weight or less, more preferably 0.25% by weight or less, further more preferably 0.2% by weight or less, still more preferably 0.15% by weight or less, calculated to the total weight of the composition.

For attaining the above-mentioned effects, it is preferred that the total concentration of compounds according to b) is in the range of 0.001% to 0.5% by weight, preferably in the range of 0.005% to 0.25% by weight, more preferably in the range of 0.01% to 0.2% by weight, still more preferably in the range of 0.03% to 0.15% by weight, calculated to the total weight of the composition.

It is preferred from the viewpoint of stabilization performance that the weight ratio of compounds a) to b) is 2 or more, more preferably 20 or more, further more preferably 37.5 or more, further more preferably 100 or more.

It is preferred from the viewpoint of stabilization performance that the weight ratio of compounds a) to b) is 1,000 or less, more preferably 600 or less, further more preferably 400 or less, further more preferably 150 or less.

For achieving the above-mentioned effects, it is preferred that the weight ratio of compounds a) to b) is in the range of 2 to 1,000, more preferably in the range of 20 to 600, further more preferably in the range of 37.5 to 400, further more preferably in the range of 100 to 150.

Preferably, composition A is a non-dyeing composition. A non-dyeing composition within the meaning of the present invention is a composition, which does not comprise sufficient amount of dyes to color keratin fibers as judged with the naked human eye.

Form of Aqueous Oxidizing Composition

The composition of the present invention preferably is an emulsion, thickened gel, or a combination thereof, from the viewpoint of cosmetic safety as well as user friendliness.

Lipophilic Compounds as Compounds According to Group c)

In case the composition of the present invention is formulated as an emulsion and/or thickened emulsion, it is preferred that the composition comprises one or more lipophilic compound(s) as compound(s) according to group c).

Preferably, compounds according to group c) are selected from $C_{12}$ to $C_{22}$ fatty alcohols, esters of $C_3$ to $C_{22}$ alcohols with $C_{12}$ to $C_{22}$ fatty acids, $C_8$ to $C_{22}$ fatty acids, vegetable oils, and/or silicones, and/or hydrocarbon-based products, and/or their mixtures, from the viewpoint of cosmetic compatibility.

Suitable $C_{12}$ to $C_{22}$ fatty alcohols are myristyl alcohol, cetyl alcohol, stearyl alcohol, behenyl alcohol, and cetearyl alcohol.

Suitable esters of $C_3$ to $C_{22}$ alcohols with $C_{12}$ to $C_{22}$ fatty acids are isopropyl myristate, isopropyl palmitate, and myristyl myristate.

Suitable $C_8$ to $C_{22}$ fatty acids are oleic acid, linoleic acid, and palmitic acid.

Suitable vegetable oils are olive oil, almond oil, sunflower oil, and argan oil.

Suitable silicones are non-aminated and/or aminated silicones. The latter are commonly known as amodimethicones.

It is preferred from the viewpoint of forming a stable composition and user friendliness that the total concentration of compounds according to group c) is 1% by weight or more, more preferably 2% by weight or more, further more preferably 3% by weight or more, calculated to the total weight of the composition.

It is preferred from the viewpoint of forming a stable composition that the total concentration of compounds according to group c) is 20% by weight or less, more preferably 15% by weight or less, further more preferably 12% by weight or less, calculated to the total weight of the composition.

For attaining the above-mentioned effects, the total concentration of compounds according to group c) is in the range of 1% to 20% by weight, preferably in the range of 2% to 15% by weight, more preferably in the range of 3% to 12% by weight, calculated to the total weight of the composition.

Surfactants as Compounds According to Group d)

The composition of the present invention may further comprise one or more surfactant(s) as compound(s) according to group d), preferably selected from non-ionic surfactants, anionic surfactants, cationic surfactants, and/or amphoteric/zwitterionic surfactants, and/or their salt(s), and/or their mixtures, more preferably selected from anionic surfactants and/or their salt(s), from the viewpoint of stabilizing the composition and improving wettability and mixability.

Preferably, the anionic surfactants may be selected from ethoxylated or non-ethoxylated alkyl ether sulfate surfactants, alkyl sulfates, ethoxylated and/or non-ethoxylated alkyl carboxylates, ethoxylated or non-ethoxylated amino acid surfactants, and/or their mixtures, and/or their salts.

Suitable examples are alkyl sulfate or preferably ethoxylated alkyl ether sulfate surfactants or mixtures thereof, and/or salts thereof, having an alkyl chain length of $C_{10}$ to $C_{22}$ and an ethoxylation degree from 1 to 50.

Suitable non-ionic surfactants may be selected from alkyl polyglycosides, ethoxylated triglycerides, ethoxylated fatty alcohols, ethoxylated fatty acid esters, and/or their mixtures.

Suitable cationic surfactants are quaternary ammonium surfactants having a carbon chain length in the range of $C_{12}$ to $C_{22}$ or surfactants having a tertiary amine group and at least one alkyl chain having a carbon chain length in the range of $C_{12}$ to $C_{22}$ such as alkylamidoalkylamine surfactants, and/or their salts. Suitable examples are cetrimonium chloride and behentrimonium chloride.

Suitable amphoteric/zwitterionic surfactants are of betaine type. Suitable compounds may be selected from alkyl betaines and/or alkylamido betaines. A preferred compound selected from alkyl betaines is lauryl betaine. A preferred compound selected from alkylamido betaines is cocamidopropyl betaine. The disclosure also relates to the salts of the compounds.

Suitable concentration ranges for surfactants as compound(s) according to group d) are in the range of 0.1% to 10% by weight, calculated to the total weight of the composition, from the viewpoint of enhancing wettability of keratin fibers, physical stability, and mixability with other compositions.

Thickening Polymers

From the viewpoint of cosmetic safety, it is further preferred that the composition of the present invention comprises one or more thickening polymer as compound(s) according to group e).

The composition of the present invention comprises one or more thickening polymer(s) as compound(s) according to group e) is/are selected from non-ionic thickening polymers and/or anionic thickening polymers, and/or their mixtures, and/or their salt(s).

Preferably, the thickening polymers are selected from polymers resulting in an aqueous solution and/or aqueous dispersion at pH between 1 and 6 having a viscosity of at least 1,000 mPa·s measured at a polymer concentration of 1% by weight in water at 25° C., calculated to the total weight of the composition, determined by a Brookfield viscometer, such as at 10 rpm for 1 min, with an appropriate spindle at 25° C.

Suitable non-ionic thickening polymers are cellulose-based polymers. Suitable examples of cellulose-based polymers are methylcellulose, hydroxymethylcellulose, hydroxyethylcellulose, hydroxypropylcellulose, hydroxyethyl-methylcellulose, and alkylated hydroxyl celluloses such as $(C_2-C_8)$-alkylcelluloses or cetyl hydroxyethylcellulose.

Suitable anionic thickening polymers are selected from naturally-based anionic polymers and/or synthetic anionic polymers.

Suitably, the natural anionic polymer(s) may be selected from xanthan gum, dehydroxanthan gum, hydroxypropylxanthan gum, carboxymethyl cellulose and starch based polymers such as vegetable starch and/or their synthetically modified derivatives such as hydroxypropyl starch phosphate. Equally suitable are alginic acids, sodium alginates, ammonium alginates, calcium alginates, gum arabic, and guar gum.

Suitable synthetic anionic polymers are associative thickening polymers, such as acrylates/steareth-30 methacrylate copolymer.

The preferred thickening polymer for the composition of the present invention are natural anionic polymers, more preferably xanthan gum and/or dehydroxanthan gum, from the viewpoint of their biodegradability and low environmental impact.

Preferably, the total concentration of thickening polymers as compound(s) according to group e) in the composition are 0.1% by weight or more, more preferably 0.25% by weight or more, more preferably 0.5% by weight or more, calculated to the total weight of the composition, from the viewpoint of providing sufficient viscosity to the composition.

Preferably, the total concentration of thickening polymers as compound(s) according to group e) in the composition are 15% by weight or less, more preferably 12% by weight or more, further more preferably 10% by weight or less, calculated to the total weight of the composition, from the viewpoint of providing sufficient viscosity to the composition and cost of goods.

For attaining the above-mentioned effects, it is preferred that the total concentration of thickening polymers as compound(s) according to group e) in the composition of the present invention is in the range of 0.1% to 15% by weight, preferably in the range of 0.25% to 12% by weight, more preferably in the range of 0.5% to 10% by weight, calculated to the total weight of the composition.

It is preferred from the viewpoint of cosmetic safety that the composition of the present invention has a viscosity in the range of 1,000 Pas to 25,000 mPas, preferably 2,000 mPas to 20,000 mPas, more preferably in the range of 2,500 mPas to 17,500 mPas, determined by cone plate viscometry at 25° C. under atmospheric conditions. A suitable viscometer is a Brookfield viscometer with spindle #4.

Kit-of-Parts

The present invention is also directed to a kit-of-parts comprising composition A as defined above and one more composition selected from:
- a bleaching composition B comprising one or more persalt(s) and/or peroxy salt(s) and one or more alkalizing agent(s),
- an aqueous lightening composition C comprising one or more alkalizing agent(s) and having a pH in the range of 7 to 12,
- an aqueous dyeing composition D having a pH in the range of 7 to 12 and comprising one or more dye selected from oxidative dye precursor(s), oxidative dye coupler(s), and/or direct dye(s), and/or their salt(s), and/or their mixtures.
- an aqueous permanent waving composition E having a pH in the range of 3 to 12 comprising one or more reducing agent(s) and one or more alkalizing agent(s).

It is preferred from the viewpoint of customer friendliness that the aforementioned compositions are separately packed.

Bleaching Composition B

It is further preferred that the bleaching composition B comprises one or more persalt(s) and/or peroxy salt(s) and one or more alkalizing agent(s).

The bleaching composition B comprises one or more persalt(s) and/or peroxy salt(s). Suitable persalts and/or peroxy salts are sodium persulfate, potassium persulfate, ammonium persulfate, earth alkali peroxides such as magnesium peroxide, melamine peroxide or urea peroxide or phthalimidoperoxy hexanoic acid. The preferred persalts from the viewpoint of bleaching power are sodium, potassium and ammonium persulfate.

It is preferred from the viewpoint of bleaching power and cosmetic safety that the total concentration of persalts and/or peroxy salts in the bleaching composition B is in the range of 10% to 80% by weight, preferably in the range of 15% to 70% by weight, more preferably in the range of 20% to 60% by weight, and still more preferably in the range of 25% to 60% by weight, calculated to the total weight of the bleaching composition B.

The bleaching composition B further comprises one or more alkalizing agent(s). Suitable alkalizing agent(s) are metasilicates and disilicates, in particular sodium metasilicate or sodium disilicate, and/or their mixtures. It is preferred from the viewpoint of alkalinity that the concentration of metasilicates and/or disilicates in the bleaching composition B is in the range of 1% to 20% by weight, more preferably 5% to 15% by weight, calculated to the total weight of the bleaching composition B.

Other suitable alkalizing agent(s) are carbonate and bicarbonate alkali salts such as sodium, potassium, and ammonium salts. The preferred salts are bicarbonate salts and especially preferred is ammonium bicarbonate, from the viewpoint of buffer capacity. Suitable concentration of carbonates in the bleaching composition B is in the range of 0.25% to 10% by weight, preferably in the range of 0.5% to 7.5% by weight, more preferably in the range of 0.75% to 5% by weight, and still more preferably in the range of 1% to 4% by weight, calculated to the total weight of the bleaching composition B, from the viewpoint of buffer capacity and low hair damage.

It is preferred from the viewpoint of user convenience that the bleaching composition B is a bleaching powder composition and comprises less than 10% by weight of water, calculated to the total weight of the bleaching composition B, preferably it is anhydrous.

In another aspect, it is preferred from the viewpoint of user convenience that the bleaching composition B is a bleach oil composition comprising one or more compound(s) according to group c).

Suitably, such bleach oil compositions comprise water at 40% by weight or less, preferably at 30% by weight or less, more preferably at 20% by weight or less, further more preferably at 10% by weight or less, calculated to the total weight of the bleaching composition B, still further more preferably it is anhydrous.

Aqueous Lightening Composition C

Preferably, the aqueous lightening composition C is an emulsion comprising one or more lipophilic compound according to group c), as also disclosed for the aqueous oxidizing composition A, from the viewpoint of user convenience.

The aqueous lightening composition preferably has a pH in the range of 8 to 11, more preferably in the range of 8.5 to 10.5, from the viewpoint of lightening performance. Suitable alkalizing agents are disclosed below for the aqueous dyeing composition D.

Aqueous Dyeing Composition D

The aqueous dyeing composition D may comprise oxidative dye precursors, for example, p-phenylendiamine and/or its derivatives, p-aminophenol and/or its derivatives, and heterocyclic compounds such as diaminopyrazols and substituted pyrimidines and/or their derivatives and/or their salts.

Furthermore, besides oxidative dye precursors, aqueous dyeing composition D may comprise oxidative dye couplers. Suitable oxidative dye couplers are resorcinol and/or its derivatives, m-aminophenol and/or its derivatives, m-phenylenediamine and/or its derivatives, pyridines and/or its derivatives, and naphthol and/or its derivatives, and/or their salts.

Furthermore, the aqueous dyeing composition D may comprise one or more hair direct dye(s).

The suitable total concentration of oxidative dye precursors and/or oxidative dye couplers and/or direct dyes is in the range of 0.001% to 5% by weight, preferably in the range of 0.01% to 4% by weight, more preferably in the range of 0.05% to 3% by weight, still more preferably in the range of 0.1% to 2% by weight, calculated to the total weight of the aqueous dyeing composition D.

Suitably, the aqueous dyeing composition D comprises one or more alkalizing agent. Preferably, one or more alkalizing agent(s) is selected from ammonia, alkyl- or alkanolamines according to the general structure

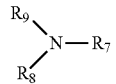

wherein $R_7$, $R_8$, and $R_9$ are same or different H, from $C_1$ to $C_4$ alkyl, $C_3$ to $C_4$ unsaturated alkyl, $C_3$ to $C_4$ branched alkyl, $C_1$ to $C_4$ hydroxyl alkyl, $C_3$ to $C_4$ unsaturated hydroxyl alkyl, $C_3$ to $C_4$ branched hydroxyl alkyl, with the condition that at least one of $R_7$, $R_8$, or $R_9$ is different from H.

It is preferred from the viewpoint of dyeing intensity that the alkalizing agent is selected from ammonia and/or monoethanolamine and/or 2-aminomethyl propanol and/or tris-(hydroxymethyl)-aminomethane.

It is further preferred from the viewpoint of sufficient alkalinity and dyeing intensity that the total concentration of alkalizing agents in the aqueous dyeing composition D is in the range of 0.25% to 15% by weight, more preferably in the range of 0.5% to 12.5% by weight, still more preferably in the range of 0.75% to 10% by weight, and still more preferably in the range of 1% to 7.5% by weight, calculated to the total weight of the aqueous dyeing composition D.

The aqueous dyeing composition D has a pH in the range of 7 to 12. It is preferred from the viewpoint of buffering capacity that the pH of the aqueous dyeing composition D is in the range of 7.5 to 11, more preferably in the range of 8.0 to 10, still more preferably in the range of 8.5 to 9.5.

Aqueous Permanent Waving Composition E

The aqueous permanent waving composition E has a pH in the range of 3 to 12 and comprises one or more reducing agent(s) and one or more alkalizing agent(s).

The aqueous permanent waving composition E comprises one or more reducing agent(s). In principle, any inorganic or organic reducing agent and/or their mixtures are suitable for the purpose of the present invention.

Suitable inorganic reducing agents are sulfite and/or hydrogen sulfite salts such as sodium, potassium, and ammonium salts. Suitable organic reducing agents are thiogylcolic acid and/or its salts, cysteamine and/or its salts, thioglycerin and/or its salts, glycerin esters of thioglycolic acid and/or its salts, thiolactic acid and/or its salts, cysteine or its derivatives and/or its salts, and/or their mixtures. Preferred are thioglycolic acid and/or its salts, thiolactic acid and/or its salts, cysteine or its derivatives and/or its salts and sodium, potassium, ammonium sulfites and their mixtures, form the viewpoint of cosmetic safety. The most preferred reducing agents are thioglycolic acid and/or its salts and sodium, potassium, ammonium sulfites and/or their mixtures, form the viewpoint of cosmetic safety.

It is preferred that the total concentration of reducing agents in the aqueous permanent waving composition E is in the range of 0.5% to 20% by weight, more preferably 1% to 15% by weight, still more preferably 2% to 12% by weight, and still more preferably 3% to 10% by weight, calculated to the total weight of the aqueous permanent waving composition E.

The pH of the composition may be acidic or alkaline and is in the range of 3 to 12, preferably 4 to 11, and most preferably it is alkaline and in the range of 7.5 to 10.5, from the viewpoint of reducing power. The pH may be adjusted with the known organic and/or inorganic acids and alkalizing agents as disclosed for the aqueous dyeing composition D.

Method for Bleaching and/or Lightening

The present invention is also directed to a method for bleaching and/or lightening of keratin fibers, preferably human keratin fibers, more preferably human hair comprising the steps of:
  i) providing composition A as defined above,
  ii) mixing composition A with a bleaching composition B or an aqueous lightening composition C as defined above to prepare a ready-to-use composition having a pH in the range of 7 to 12,
  iii) applying the ready-to-use composition onto keratin fibers and leaving it for a time period in the range of 1 to 60 min,
  iv) rinsing off the keratin fibers and optionally shampooing the keratin fibers.

The bleaching composition B or aqueous lightening composition C of step ii) is then mixed with composition A of the present invention according to step ii) to form a ready-to-use composition. Suitable mixing ratios by weight are 5:1 to 1:5 (bleaching composition B/aqueous lightening composition C: composition A). Customarily, suitable mixing ratios are 1:1, 1:2, and 1:3 by weight (bleaching composition B/aqueous lightening composition C: composition A).

Suitably, the pH of the ready-to-use composition is in the range of 7 to 12. It is preferred from the viewpoint of accelerated dyeing that the pH of the ready-to-use composition is in the range of 7.5 to 11, more preferably 8.0 to 10.5.

The ready-to-use composition is then applied to keratin fibers and left for a time period of 1 min to 60 min as defined in step iii). Preferred time ranges for step iii) are 5 min to 45 min, more preferred ranges are 10 min to 35 min, from the viewpoint of sufficiently bleaching/lightening.

Optionally, heat may be applied while leaving the ready-to-use composition onto keratin fibers. Suitable temperature ranges are 30° C. to 50° C.

After that, the ready-to-use composition is rinsed-off from keratin fibers according to step iv) and optionally they are shampooed and optionally blow-dried.

Method for Dyeing

The present invention is also directed to a method for dyeing of keratin fibers, preferably human keratin fibers, more preferably human hair, comprising the steps of:
  xi) providing composition A as defined above,
  xii) mixing composition A with a dyeing composition D as defined above to prepare a ready-to-use composition having a pH in the range of 7 to 12,
  xiii) applying the ready-to-use composition onto keratin fibers and leaving it for a time period of 1 to 60 min,
  xiv) rinsing off the keratin fibers and optionally shampooing the keratin fibers.

Composition A is then mixed with the dyeing composition D in step xii) to form a ready-to-use composition. Suitable mixing ratios by weight are 5:1 to 1:5 (composition A: dyeing composition D). Customarily, suitable mixing ratios are 1:1, 1:2, and 1:3 by weight (dyeing composition D: composition A).

Suitably, the pH of the ready-to-use composition is in the range of 7 to 12. It is preferred from the viewpoint of accelerated dyeing speed that the pH of the ready-to-use composition is in the range of 7.5 to 11, more preferably 8.0 to 10.5.

The ready-to-use composition is then applied to keratin fibers and left for a time period of 1 min to 60 min as defined in step xiii). Preferred time ranges for step xiii) are 5 min to 45 min, more preferred ranges are 10 min to 35 min, from the viewpoint of sufficiently developing the hair color.

During the application time of the ready-to-use mixture, heat may be applied to the keratin fibers, preferably in a temperature range from 30° C. to 50° C., from the viewpoint of accelerating dyeing speed and cosmetic safety.

After that, the ready-to-use composition is rinsed-off from keratin fibers in step xiv) and optionally they are shampooed and optionally blow-dried.

Permanent Shaping

The present invention is also directed to a method for permanently shaping keratin fibers, preferably human keratin fibers, more preferably human hair, comprising the steps of:
xxi) optionally shampooing the keratin fibers,
xxii) putting keratin fibers under mechanical tension,
xxiii) applying to keratin fibers an aqueous permanent waving composition E as defined above, and leaving the composition for a time period in the range of 1 min to 60 min,
xxiv) optionally rinsing off the composition,
xxv) providing composition A as defined above, applying it to keratin fibers and leaving it for a time period in the range of 1 min to 30 min,
xxvi) releasing mechanical tension from keratin fibers,
xxvii) rinsing off the keratin fibers and optionally shampooing the keratin fibers,
with the provision that steps xxii) and xxiii) as well as steps xxvi) and xxvii) may be performed in any order.

The term "permanent shaping" is to be understood as referring to permanent curling and permanent straightening.

Thus, mechanical tension as defined in step xxii) is, for example, provided by putting the keratin fibers on curlers or by straightening the fibers by comb and brush.

Composition A is then applied to hair in step xxv) and left for a time period of 1 min to 30 min. It is preferred from the viewpoint of hair damage and oxidation performance that the composition is left on keratin fibers for 2 min to 25 min, more preferably for 3 min to 20 min, and further more preferably for 5 min to 15 min, optionally while applying heat and/or under use of heating device.

Use of Compounds

The present invention is also directed to a use of one or more compound(s) selected from
1) one or more orthodiphenol(s) and/or their derivatives, and/or their mixtures, and/or their salt(s),
2) one or more imidazolidin-2,4-dione(s) and/or their derivatives, and/or their mixtures, and/or their salt(s), for improving storage stability of aqueous compositions comprising hydrogen peroxide.

It is preferred from the viewpoint of stabilization that one or more compound (s) according to 1) is one or more compound(s) as defined as b1) above.

It is preferred from the viewpoint of stabilization that one or more compound (s) according to 2) is one or more compound(s) as defined as b2) above.

The present disclosure is also directed to <1> an aqueous oxidizing composition A having a pH in the range of 1 to 6 comprising:
a) hydrogen peroxide, and
b) one or more compound(s) selected from:
1) one or more orthodiphenol(s) and/or their derivatives, and/or their mixtures, and/or their salt(s),
2) one or more imidazolidin-2,4-dione(s) and/or their derivatives, and/or their mixtures, and/or their salt(s).

<2> The composition according to clause <1> characterized in that one or more compound(s) according to group b1) is selected from
Flavonols,
Anthocyanidines,
Anthocyanines or anthocyanes,
Orthohydroxybenzoates,
Flavones,
Hydroxystilbenes,
3,4-dihydroxyphenylalanine and its derivatives,
2,3-dihydroxyphenylalanine and its derivatives,
4,5-dihydroxyphenylalanine and its derivatives,
Dihydroxycinnamates,
Orthopolyhydroxycoumarines,
Orhtopolyhydroxyisocoumarines,
Orthopolyhydroxycoumarones,
Orthopolyhydroxyisocoumarones,
Orhtopolyhydroxychalcones,
Orhtopolyhydroxychromones,
Orhtopolyhydroxyquinones,
Orhtohydroxyxanthones,
1,2-dihyroxybenzenes and its derivatives,
1,2,4-trihydroxybenzenes and its derivatives,
1,2,3-trihydroxybenzenes and its derivatives,
2,4,5-trihydroxybenzenes and its derivatives,
Proanthocyanidines,
Proanthocyanines,
Tannic acid,
Ellagic acid,
one or more compound(s) according to the following general structure:

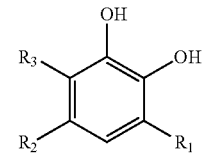

wherein $R_1$, $R_2$, and $R_3$ are independently selected from H, OH, halogen, $C_1$-$C_{12}$ linear or branched alkyl or alkenyl, O—X, $NO_2$, COOH, $SO_3H$, aryl, heteroaryl, and/or their salt(s), and/or their mixtures, with X being $C_1$-$C_{12}$ linear or branched alkyl.
and/or their salt(s), and/or their mixture(s).

<3> The composition according to any of the clauses <1> to <2> characterized in that one or more compound(s) according to group b1) is selected from the following general structure:

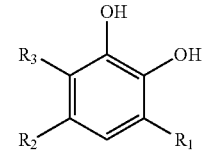

wherein $R_1$, $R_2$, and $R_3$ are independently selected from H, OH, halogen, $C_1$-$C_{12}$ linear or branched alkyl or alkenyl, O—X, $NO_2$, COOH, $SO_3H$, aryl, heteroaryl, and/or their salt(s), and/or their mixtures, with X being $C_1$-$C_{12}$ linear or branched alkyl.

<4> The composition according to any of the clauses <1> and/or <3> characterized in that for group b1) $R_1$ is selected from H, OH, halogen, $C_1$-$C_{12}$ linear or branched alkyl or alkenyl, O—X, $NO_2$, COOH, $SO_3H$, aryl, heteroaryl, with X being $C_1$-$C_{12}$ linear or branched alkyl, and $R_2$, and $R_3$ are independently selected from $C_1$-$C_{12}$ linear or branched alkyl or alkenyl, O—X, $NO_2$, COOH, $SO_3H$, and/or their salt(s), and/or their mixtures, with X being $C_1$-$C_{12}$ linear or branched alkyl.

<5> The composition according to any of the clauses <1> to <4> characterized in that at least one compound according to group b1) is selected from:

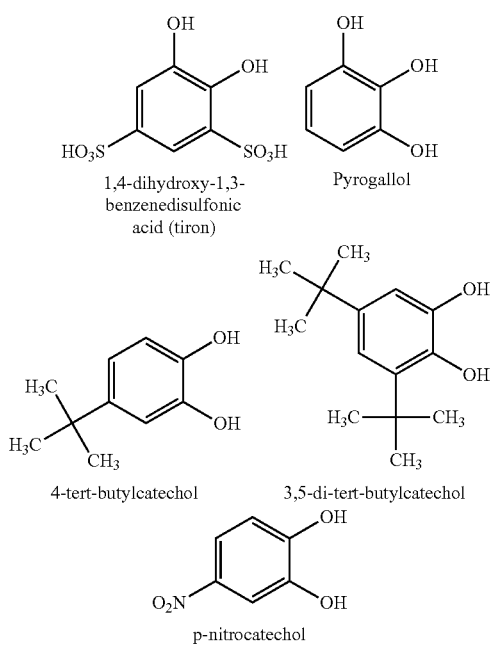

1,4-dihydroxy-1,3-benzenedisulfonic acid (tiron)

Pyrogallol 4-tert-butylcatechol 3,5-di-tert-butylcatechol p-nitrocatechol and/or their salt(s), and/or their mixtures.

<6> The composition according to any of the clauses <1> to <5> characterized in that one more compound(s) according to group b1) is tiron and/or its salt(s).

<7> The composition according to any of the clauses <1> to <6> characterized in that the total concentration of compounds according to b1) is in the range of 0.001% to 0.5% by weight, preferably in the range of 0.005% to 0.25% by weight, more preferably in the range of 0.01% to 0.2% by weight, still more preferably in the range of 0.03% to 0.15% by weight, calculated to the total weight of the composition.

<8> The composition according to any of the clauses <1> to <7> characterized in that the total concentration of tiron and/or its salt(s) is in the range of 0.001% to 0.5% by weight, preferably in the range of 0.005% to 0.25% by weight, more preferably in the range of 0.01% to 0.2% by weight, still more preferably in the range of 0.03% to 0.15% by weight, calculated to the total weight of the composition.

<9> The composition according to clause <1> characterized in that one or more compound(s) according to group b2) is according to the following general structure:

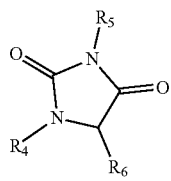

wherein $R_4$, $R_5$, and Re are independently selected from H, OH, halogen, $C_1$-$C_{12}$ linear or branched alkyl or alkenyl, O—X, COOH, phenyl, diphenyl, ureyl, and/or their salt(s), and/or their mixtures, with X being $C_1$-$C_{12}$ linear or branched alkyl.

<10> The composition according to any of the clauses <1> and/or <9> characterized in that one or more compound(s) according to group b2) is:

hydantoin,
dichlordimethylhydantoin,
bromchlordimethylhydantoin,
dibromdimethylhydantoin,
ethotoin,
phenytoin,
mephenytoin,
fosphenytoin,
allantoin,
and/or their salt(s), and/or their mixtures.

<11> The composition according to any of the clauses <1> and/or <9> to <10> characterized in that one or more compound(s) according to group b2) is hydantoin or allantoin, and/or their salt(s), and/or their mixtures.

<12> The composition according to any of the clauses <1> and/or <9> to <11> characterized in that one or more compound(s) according to group b2) is hydantoin and/or its salt(s).

<13> The composition according to any of the clauses <1> and/or <9> to <12> characterized in that the total concentration of compounds according to b2) is in the range of 0.001% to 0.5% by weight, preferably in the range of 0.005% to 0.25% by weight, more preferably in the range of 0.01% to 0.2% by weight, still more preferably in the range of 0.03% to 0.15% by weight, calculated to the total weight of the composition.

<14> The composition according to any of the clauses <1> and/or <9> to <13> characterized in that the total concentration of hydantoin and/or its salt(s) is in the range of 0.001% to 0.5% by weight, preferably in the range of 0.005% to 0.25% by weight, more preferably in the range of 0.01% to 0.2% by weight, still more preferably in the range of 0.03% to 0.15% by weight, calculated to the total weight of the composition.

<15> The composition according to any of the clauses <1> to <14> characterized in that the total concentration of compounds according to b) is in the range of 0.001% to 0.5% by weight, preferably in the range of 0.005% to 0.25% by weight, more preferably in the range of 0.01% to 0.2% by weight, still more preferably in the range of 0.03% to 0.15% by weight, calculated to the total weight of the composition.

<16> The composition according to any of the clauses <1> to <15> characterized in that the pH of the composition is in the range of 1.25 to 5, more preferably in the range of 1.5 to 4, further more preferably in the range of 2 to 3.

<17> The composition according to any of the clauses <1> to <16> characterized in that the concentration of the compound according to a) is in the range of 0.1% to 20% by weight, preferably in the range of 0.5% to 15% by weight, more preferably in the range of 1% to 12% by weight, further more preferably in the range of 3% to 12% by weight, calculated to the total weight of the composition.

<18> The composition according to any of the clauses <1> to <17> characterized in that the weight ratio of compounds a) to b) is in the range of 2 to 1,000, more preferably in the range of 20 to 600, further more preferably in the range of 37.5 to 400, further more preferably in the range of 100 to 150.

<19> The composition according to any of the clauses <1> to <8> and/or <15> to <17> characterized in that the weight ratio of compounds a) to b1) is in the range of 2 to 1,000, more preferably in the range of 20 to 600, further more preferably in the range of 37.5 to 400, further more preferably in the range of 100 to 150.

<20> The composition according to any of the clauses <1> and/or <9> to <17> characterized in that the weight ratio of compounds a) to b2) is in the range of 2 to 1,000, more preferably in the range of 20 to 600, further more preferably in the range of 37.5 to 400, further more preferably in the range of 100 to 150.

<21> The composition according to any of the clauses <1> to <20> characterized in that it is a non-dyeing composition.

<22> The composition according to any of the clauses <1> to <21> characterized in that it is a thickened gel and/or an emulsion.

<23> The composition according to any of the clauses <1> to <22> characterized in that the composition comprises one or more lipophilic compound(s) as compound(s) according to group c).

<24> The composition according to clause <23> characterized in that the compound according to group c) is selected from $C_{12}$ to $C_{22}$ fatty alcohols, esters of $C_3$ to $C_{22}$ alcohols with $C_{12}$ to $C_{22}$ fatty acids, $C_8$ to $C_{22}$ fatty acids, vegetable oils, and/or silicones, and/or hydrocarbon-based products, and/or their mixtures.

<25> The composition according to any of the clauses <23> and/or <24> characterized in that the total concentration of compounds according to group c) is in the range of 1% to 20% by weight, preferably in the range of 2% to 15% by weight, more preferably in the range of 3% to 12% by weight, calculated to the total weight of the composition.

<26> The composition according to any of the clauses <1> to <25> characterized in that it comprises one or more surfactant(s) as compound according to group d), preferably selected from non-ionic surfactants, anionic surfactants, cationic surfactants, and/or amphoteric/zwitterionic surfactants, and/or their salt(s), and/or their mixtures, more preferably selected from anionic surfactants and/or their salt(s).

<27> The composition according to clause <26> characterized in that the total concentration of one or more compound(s) according to group d) is in the range of 0.1% to 10% by weight, calculated to the total weight of the composition.

<28> The composition according to any of the clauses <1> to <27> characterized in that the composition comprises one or more thickening polymer as compound(s) according to group e).

<29> The composition according to clause <28> characterized in that one or more thickening polymer(s) according to group e) is/are selected from non-ionic thickening polymers and/or anionic thickening polymers, and/or their mixtures, and/or their salt(s).

<30> The composition according to any of the clauses <28> and/or <29> characterized in that the total concentration of thickening polymers as compound(s) according to group e) is in the range of 0.1% to 15% by weight, preferably in the range of 0.25% to 12% by weight, more preferably in the range of 0.5% to 10% by weight, calculated to the total weight of the composition.

The present disclosure is also directed to <31> a kit-of-parts comprising composition A as defined in any of the clauses <1> to <30> and one more composition selected from:
 a bleaching composition B comprising one or more persalt(s) and/or peroxy salt(s) and one or more alkalizing agent(s),
 an aqueous lightening composition C comprising one or more alkalizing agent(s) and having a pH in the range of 7 to 12,
 an aqueous dyeing composition D having a pH in the range of 7 to 12 and comprising one or more dye selected from oxidative dye precursor(s), oxidative dye coupler(s), and/or direct dye(s), and/or their salt(s), and/or their mixtures.
 an aqueous permanent waving composition E having a pH in the range of 3 to 12 comprising one or more reducing agent(s) and one or more alkalizing agent(s).

<31> The kit-of-parts according to clause <30> characterized in that the compositions are separately packed.

<32> The kit-of-parts according to any of the clauses <30> and/or <31> characterized in that the total concentration of persalts and/or peroxy salts in the bleaching composition B is in the range of 10% to 80% by weight, preferably in the range of 15% to 70% by weight, more preferably in the range of 20% to 60% by weight, and still more preferably in the range of 25% to 60% by weight, calculated to the total weight of the bleaching composition B.

<33> The kit-of-parts according to any of the clauses <30> to <32> characterized in that the bleaching composition B is a bleaching powder composition and comprises less than 10% by weight of water, calculated to the total weight of the bleaching composition B, preferably it is anhydrous.

<34> The kit-of-parts according to clause <33> characterized in that the alkalizing agent(s) of the bleaching composition B is/are metasilicates and/or disilicates, and/or its/their salt(s), preferably sodium metasilicate or sodium disilicate, and/or their mixtures.

<35> The kit-of-parts according to clauses <34> characterized in that the concentration of metasilicates and/or disilicates and/or their salt(s) in the bleaching composition B is in the range of 1% to 20% by weight, more preferably 5% to 15% by weight, calculated to the total weight of the bleaching composition B.

<36> The kit-of-parts according to any of the clauses <30> to <32> and/or <34> to <35> characterized in that the bleaching composition B is a bleach oil composition comprising one or more compound(s) according to group c).

<37> The kit-of-parts according to clause <36> characterized in that the bleach oil composition comprises water at 40% by weight or less, preferably at 30% by weight or less, more preferably at 20% by weight or less, further more preferably at 10% by weight or less, calculated to the total weight of the bleaching composition B, still further more preferably it is anhydrous.

<38> The kit-of-parts according to any of the clauses <30> to <31> characterized in that the aqueous lightening composition C is an emulsion comprising one or more lipophilic compound according to group c).

<39> The kit-of-parts according to any of the clauses <30>, <31>, and <38> characterized in that the aqueous lightening composition C has a pH in the range of 8 to 11, more preferably in the range of 8.5 to 10.5.

<40> The kit-of-parts according to any of the clauses <30> and/or <31> characterized in that the aqueous dyeing composition D comprises oxidative dye precursors, preferably p-phenylendiamine and/or its derivatives, p-aminophenol and/or its derivatives, and heterocyclic compounds such as diaminopyrazols and substituted pyrimidines, and/or their derivatives, and/or their salts.

<41> The kit-of-parts according to any of the clauses <30> to <31>, and <40> characterized in that the aqueous dyeing composition D comprises oxidative dye couplers, preferably resorcinol and/or its derivatives, m-aminophenol and/or its derivatives, m-phenylenediamine and/or its derivatives, pyridines and/or its derivatives, and naphthol and/or its derivatives, and/or their salts.

<42> The kit-of-parts according to any of the clauses <30> to <31>, and <40> to <41> characterized in that the aqueous dyeing composition D comprises one or more hair direct dye(s).

<43> The kit-of-parts according to any of the clauses <30> to <31>, and <40> to <42> characterized in that the total concentration of oxidative dye precursors and/or oxidative dye couplers and/or direct dyes is in the range of 0.001% to 5% by weight, preferably in the range of 0.01% to 4% by weight, more preferably in the range of 0.05% to 3% by weight, still more preferably in the range of 0.1% to 2% by weight, calculated to the total weight of the aqueous dyeing composition D.

<44> The kit-of-parts according to any of the clauses <30> to <31>, and <40> to <43> characterized in that the aqueous dyeing composition D comprises one or more alkalizing agent, preferably one or more alkalizing agent(s) selected from ammonia, alkyl- or alkanolamines according to the general structure

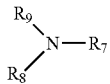

wherein $R_7$, $R_8$, and $R_9$ are same or different H, from $C_1$ to $C_4$ alkyl, $C_3$ to $C_4$ unsaturated alkyl, $C_3$ to $C_4$ branched alkyl, $C_1$ to $C_4$ hydroxyl alkyl, $C_3$ to $C_4$ unsaturated hydroxyl alkyl, $C_3$ to $C_4$ branched hydroxyl alkyl, with the condition that at least one of $R_7$, $R_8$, or $R_9$ is different from H.

<45> The kit-of-parts according to any of the clauses <30> to <31>, and <40> to <44> characterized in that one or more alkalizing agent of the aqueous dyeing composition D is selected from ammonia and/or monoethanolamine and/or 2-aminomethyl propanol, tris-(hydroxymethyl)-aminomethane, and/or their salt(s), and/or their mixtures.

<46> The kit-of-parts according to any of the clauses <30> to <31> and/or <40> to <45> characterized in that the total concentration of alkalizing agent in the aqueous dyeing composition D is in the range of 0.25% to 15% by weight, more preferably in the range of 0.5% to 12.5% by weight, still more preferably in the range of 0.75% to 10% by weight, and still more preferably in the range of 1% to 7.5% by weight, calculated to the total weight of the aqueous dyeing composition D.

<47> The kit-of-parts according to any of the clauses <30> to <31> and/or <40> to <46> characterized in that the pH of the aqueous dyeing composition D is in the range of 7.5 to 11, more preferably in the range of 8.0 to 10, still more preferably in the range of 8.5 to 9.5.

<48> The kit-of-parts according to any of the clauses <31> and/or <32> characterized in that the aqueous permanent waving composition E comprises an inorganic reducing agent, preferably it is/are sulfite and/or hydrogen sulfite salts more preferably sodium, potassium, and ammonium salts of sulfites and/or hydrogen sulfites.

<49> The kit-of-parts according to any of the clauses <31> to <32> and <48> characterized in that the aqueous permanent waving composition E comprises organic reducing agents, preferably they are thiogylcolic acid and/or its salts, cysteamine and/or its salts, thioglycerin and/or its salts, glycerin esters of thioglycolic acid and/or its salts, thiolactic acid and/or its salts, cysteine or its derivatives and/or its salts, and/or their mixtures.

<50> The kit-of-parts according to any of the clauses <31> to <32> and <48> to <49> characterized in that the total concentration of reducing agents aqueous permanent waving composition E is in the range of 0.5% to 20% by weight, more preferably 1% to 15% by weight, still more preferably 2% to 12% by weight, and still more preferably 3% to 10% by weight, calculated to the total weight of the aqueous permanent waving composition E.

<51> The kit-of-parts according to any of the clauses <31> to <32> and <48> to <50> characterized in that the pH of aqueous permanent waving composition E is in the range of 3 to 12, preferably in the range of 4 to 11, and most preferably in the range of 7.5 to 10.5.

The present disclosure is also directed to <52> a method for bleaching and/or lightening of keratin fibers, preferably human keratin fibers, more preferably human hair comprising the steps of:
 i) providing an aqueous oxidizing composition A as defined in any of the clauses <1> to <30>,
 ii) mixing composition A with a bleaching composition B or an aqueous lightening composition C as defined in any of the clauses <31> to <37> or <38> to <39> to prepare a ready-to-use composition having a pH in the range of 7 to 12,
 iii) applying the ready-to-use composition onto keratin fibers and leaving it for a time period in the range of 1 to 60 min,
 iv) rinsing off the keratin fibers and optionally shampooing the keratin fibers.

<53> The method according to clause <52> characterized in that the pH of the ready-to-use composition is in the range of 7 to 12, more preferably in the range of 7.5 to 11, further more preferably in the range of 8.0 to 10.5.

<54> The method according to any of the clauses <52> to <53> characterized in that the ready-to-use composition as defined in step iii) is left for a time period of 1 min to 60 min, preferably for a time period of 5 min to 45 min, more preferably for a time period of 10 min to 35 min.

<55> The method according to any of the clauses <52> to <54> characterized in that heat may be applied, preferably in the range of 30° C. to 50° C., while leaving the ready-to-use composition onto keratin fibers in step iii).

The present disclosure is also directed to <56> a method for dyeing of keratin fibers, preferably human keratin fibers, more preferably human hair, comprising the steps of:
 xi) providing composition A as defined in any of the clauses <1> to <30>
 xii) mixing composition A with a dyeing composition D as defined in any of the clauses <30> to <31> and <40> to <47> to prepare a ready-to-use composition having a pH in the range of 7 to 12,
 xiii) applying the ready-to-use composition onto keratin fibers and leaving it for a time period of 1 to 60 min,
 xiv) rinsing off the keratin fibers and optionally shampooing the keratin fibers.

<56> The method according to clause <55> characterized in that the ready-to-use composition of steps xii) and xiii) has a pH in the range of 7 to 12, preferably in the range of 7.5 to 11, more preferably in the range of 8.0 to 10.5.

<57> The method according to any of the clauses <55> to <56> characterized in that ready-to-use composition in step xiii) is left onto keratin fibers for a time period of 1 min to 60 min, preferably for a time period of 5 min to 45 min, more preferably for a time period of 10 min to 35 min.

<58> The method according to any of the clauses <56> to <57> characterized in that during the application time of the ready-to-use mixture, heat may be applied to the keratin fibers, preferably in a temperature range from 30° ° C. to 50° C.

The present disclosure is also directed to <59> a method for permanently shaping keratin fibers, preferably human keratin fibers, more preferably human hair, comprising the steps of:

xxi) optionally shampooing the keratin fibers,
xxii) putting keratin fibers under mechanical tension,
xxiii) applying to keratin fibers an aqueous permanent waving composition E as in any of the clauses <31> and <48> to <51>, and leaving the composition for a time period in the range of 1 min to 60 min,
xxiv) optionally rinsing off the composition,
xxv) providing composition A as defined in any of the clauses <1> to <30>, applying it to keratin fibers and leaving it for a time period in the range of 1 min to 30 min,
xxvi) releasing mechanical tension from keratin fibers,
xxvii) rinsing off the keratin fibers and optionally shampooing the keratin fibers,
with the provision that steps xxii) and xxiii) as well as steps xxvi) and xxvii) may be performed in any order.

<60> The method according to clause <59> characterized in that mechanical tension as defined in step xxii) is comprises putting the keratin fibers on curlers or straightening the fibers by comb or brush.

<61> The method according to any of the clauses <59> to <60> characterized in that in step xxv) composition A is left for a time period of 1 min to 30 min, preferably for a time period of 2 min to 25 min, more preferably for a time period of 3 min to 20 min, and further more preferably for a time period of 5 min to 15 min.

The present disclosure is also directed to <62> a use of one or more compound(s) selected from
1) one or more orthodiphenol(s) and/or their derivatives, and/or their mixtures, and/or their salt(s),
2) one or more imidazolidin-2,4-dione(s) and/or their derivatives, and/or their mixtures, and/or their salt(s), for improving storage stability of aqueous compositions comprising hydrogen peroxide.

<63> Use according to clause <62> characterized in that one or more compound (s) according to 1) is one or more compound(s) as defined as b1) in any of the clauses <1> to <8>.

<64> Use according to any of the clauses <62> to <63> characterized in that one or more compound (s) according to 2) is one or more compound(s) as defined as b2) in any of the clauses <9> to <14>.

The following examples are to illustrate the invention, but not to limit it.

EXAMPLES

The following compositions were prepared by dissolving the compounds according to group b) in an aqueous solution of hydrogen peroxide under constant stirring:

| Ingredient | | Inventive 1 | Inventive 2 | Comparative 1 |
|---|---|---|---|---|
| | | | % by weight | |
| Compound | b1) Tiron | 0.05 | — | — |
| | b2) Hydantoin | — | 0.05 | — |
| | a) Hydrogen peroxide | | 6.0 | |
| | — Phosphoric acid | | q.s. ad pH 2.5 | |
| | — Water | | Ad 100.0 | |

The compositions were prepared and stored under controlled conditions at 40° C. for 20 days. Hydrogen peroxide content was analyzed by titration and the following concentrations were measured:

| Time [days] | Inventive 1 | Inventive 2 | Comparative 1 |
|---|---|---|---|
| | | % by weight | |
| 0 | 5.96 | 5.96 | 5.96 |
| 1 | 5.91 | 5.88 | 5.86 |
| 5 | 5.90 | 5.86 | 5.09 |
| 8 | 5.88 | 5.86 | 5.07 |
| 12 | 5.88 | 5.82 | 4.71 |
| 20 | 5.86 | 5.76 | 3.48 |

As a result, the compounds according to b) could maintain more than 96% of hydrogen peroxide activity over 20 days, whereas the comparative composition without compound according to b) was only 58% active after 20 days.

Methods

Hydrogen peroxide concentration was measured by iodometric titration using a Mettler Toledo DL58 titrator equipped with a Redox electrode and a 0.1N sodium-thiosulfate-solution.

Example 3

| | % by weight |
|---|---|
| Tiron | 0.01 |
| Cetearyl alcohol | 4.0 |
| Sodium lauryl sulfate | 0.8 |
| Phosphoric acid | q.s. ad pH 1.5 |
| Tetrasodium EDTA | 0.05 |
| Hydrogen peroxide | 6.0 |
| Water | ad 100.0 |

The concentration of tiron as compound according to b) may also be adjusted to 0.05%, 0.1%, or 0.5% or any values in between to achieve the same technical effect.

The concentration of hydrogen peroxide may be adjusted to 9%, 12%, 15%, or 20% by weight, or any value in between.

Example 4

| | % by weight |
|---|---|
| Hydantoin | 0.01 |
| Cetearyl alcohol | 4.0 |
| Sodium lauryl sulfate | 0.8 |
| Phosphoric acid | q.s. ad pH 2.5 |
| Tetrasodium EDTA | 0.05 |
| Hydrogen peroxide | 6.0 |
| Water | ad 100.0 |

The concentration of hydantoin as compound according to b) may also be adjusted to 0.05%, 0.1%, or 0.5% or any values in between to achieve the same technical effect.

The concentration of hydrogen peroxide may be adjusted to 9%, 12%, 15%, or 20% by weight, or any value in between.

Example 5

| | % by weight |
|---|---|
| Tiron | 0.01 |
| Hydantoin | 0.05 |

-continued

| | % by weight |
|---|---|
| Catechol | 0.05 |
| Cetearyl alcohol | 4.0 |
| Sodium lauryl sulfate | 0.8 |
| Phosphoric acid | q.s. ad pH 3.0 |
| Tetrasodium EDTA | 0.05 |
| Hydrogen peroxide | 6.0 |
| Water | ad 100.0 |

The concentration of hydrogen peroxide may be adjusted to 9%, 12%, 15%, or 20% by weight, or any value in between.

Example 6

The following dyeing composition was prepared:

| | % by weight |
|---|---|
| Cetearyl alcohol | 12 |
| Sodium cetearyl sulfate | 2 |
| Cocamide MEA | 5 |
| Oleic acid | 2 |
| Tetrasodium EDTA | 1 |
| Sodium sulfite | 1 |
| Ammonium hydroxide | 5 |
| Ammonium chloride | 1 |
| Toluene-2,5-Diamine sulfate | 0.75 |
| Resorcinol | 0.10 |
| 4-Chlorresorcinol | 0.25 |
| m-Aminophenol | 0.05 |
| 4-Amino-2-Hydroxytoluene | 0.05 |
| HC Red 51 | 0.02 |
| Fragrance | 0.5 |
| Water | ad 100 |

The above composition had a pH of 9.9.

The oxidative dyeing composition was then mixed with the inventive composition 1 and comparative composition 1 of example 1 stored after 20 days in a weight ratio of 1:1 to yield a ready-to-use composition. The ready-to-use composition had a pH of around 9.5.

The ready-to-use compositions were applied to human hair and left for 30 min at room temperature. After that, the compositions were rinsed-off with water, the hair was shampooed, and blow-dried.

The hair was found to be intensely red-brown colored with the inventive composition 1, whereas the hair had less color intensity with the comparative composition 1.

Example 7

The following bleaching composition B was prepared:

| | % by weight |
|---|---|
| Hydroxyethylcellulose | 3 |
| Tetrasodium EDTA | 2 |
| Sodium carbonate | 1 |
| Ammonium persulfate | 11 |
| Potassium persulfate | 36 |
| Sodium metasilicate | 10 |
| Mineral oil | 8 |
| Diatomaceous Earth | to 100 |

The bleaching composition B from above was then mixed with the inventive composition 1 and comparative composition 1 of example 1 stored after 20 days at a weight ratio of 1:2 (bleaching composition B: inventive composition 1) to yield a ready-to-use composition having a pH around 9.8.

The ready-to-use compositions were then applied onto human hair and left for 30 min at room temperature. After that, the compositions were rinsed-off with water, the hair was shampooed, and blow-dried.

The hair was found to be intensely bleached with inventive composition 1, whereas the degree of lightening was visually lower for the hair streak bleached with comparative composition 1.

Example 8

The following permanent shaping composition was prepared:

| | % by weight |
|---|---|
| Ammonium thioglycolate (60%) | 21.3 |
| Ammonium hydrogen carbonate | 5.0 |
| 1,3-butylene gylcol | 3.0 |
| Amodimethicone | 0.2 |
| PEG-40-Hydrogenated castor oil | 0.7 |
| Fragrance | 0.4 |
| Ammonia (25% active) | ad pH 8.3 |
| Water | ad 100.0 |

Human hair was shampooed and the hair was put under mechanical tension on curlers. Then the composition from above was applied to hair and left for 15 min at 40° C. The composition was then rinsed-off with water.

Then the inventive composition 1 and comparative composition 1 of example 1 stored after 20 days and was applied to hair and left for 15 min at room temperature. Tension from hair was then released and the curlers were removed. The hair was then rinsed-off, shampooed, and blow-dried.

The hair was found to be intensely curled and had good cosmetic feeling with the inventive composition 1, whereas the streak treated with the comparative composition 1 had poor hair feel and less curling intensity.

The invention claimed is:

1. A composition having a pH in a range of 1 to 6, comprising:
   hydrogen peroxide; and
   one or more compounds selected from
   orthodiphenols
   imidazolidin-2,4-diones, and salts thereof,
   wherein the orthodiphenols have the following general structure:

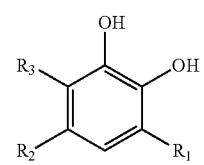

wherein $R_1$, $R_2$, and $R_3$ are independently selected from H, OH, halogen, $C_1$-$C_{12}$ linear or branched alkyl or alkenyl, O—X, $NO_2$, COOH, $SO_3H$, aryl, and heteroaryl, and X is a $C_1$-$C_{12}$ linear or branched alkyl, and wherein the imidazolidin-2,4-diones have the following general structure:

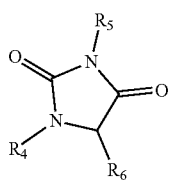

wherein $R_4$, $R_5$, and $R_6$ are independently selected from H, OH, halogen, $C_1$-$C_{12}$ linear or branched alkyl or alkenyl, O—X, COOH, phenyl, diphenyl, ureyl, and X is a $C_1$-$C_{12}$ linear or branched alkyl, wherein the composition is a non-dyeing composition.

2. The composition according to claim 1, wherein $R_1$ is selected from H, OH, halogen, $C_1$-$C_{12}$ linear or branched alkyl or alkenyl, O—X, $NO_2$, COOH, $SO_3H$, aryl, heteroaryl, and X is a $C_1$-$C_{12}$ linear or branched alkyl, and $R_2$, and $R_3$ are independently selected from C—$C_{12}$ linear or branched alkyl or alkenyl, O—X, $NO_2$, COOH, $SO_3H$, and X is a $C_1$-$C_{12}$ linear or branched alkyl.

3. The composition according to claim 1, wherein at least one of the orthodiphenols is selected from:

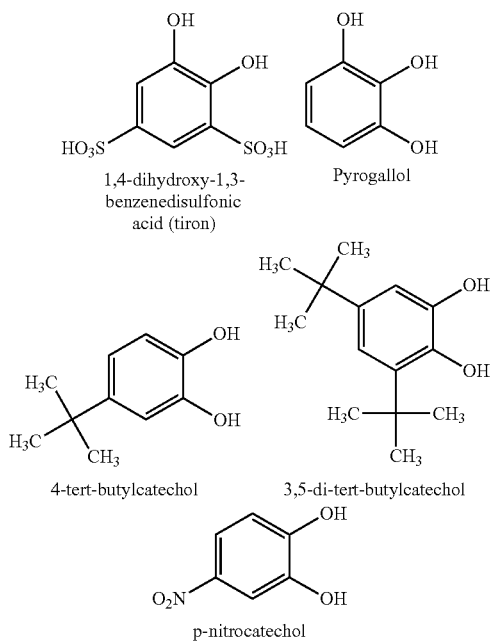

and salts thereof.

4. The composition according to claim 1, wherein at least one of the imidazolidin-2,4-diones is hydantoin, allantoin or a salt thereof.

5. The composition according to claim 1, wherein a total concentration of the one or more compounds is in a range of 0.001% to 0.5% by weight, calculated to the total weight of the composition.

6. The composition according to claim 1, further comprising one or more lipophilic compounds.

7. The composition according to claim 1, further comprising one or more surfactants.

8. A kit-of-parts, comprising:
the composition of claim 1; and
one or more compositions selected from:
a bleaching composition B comprising one or more persalts and/or peroxy salts and one or more alkalizing agents,
an aqueous lightening composition C comprising one or more alkalizing agents and having a pH in a range of 7 to 12,
an aqueous dyeing composition D having a pH in a range of 7 to 12 and comprising one or more dyes selected from oxidative dye precursors, oxidative dye couplers, direct dyes, and salts thereof, and
an aqueous permanent waving composition E having a pH in a range of 3 to 12 comprising one or more reducing agents and one or more alkalizing agents.

9. A method for bleaching, lightening and/or dyeing of keratin fibers, comprising:
mixing the composition of claim 1 with a bleaching composition B comprising one or more persalts and/or peroxy salts and one or more alkalizing agents, an aqueous lightening composition C comprising one or more alkalizing agents and having a pH in a range of 7 to 12, or an aqueous dyeing composition D having a pH in a range of 7 to 12 and comprising one or more dyes selected from oxidative dye precursors, oxidative dye couplers, direct dyes, and salts thereof, to prepare a ready-to-use composition having a pH in a range of 7 to 12;
applying the ready-to-use composition onto the keratin fibers and leaving it for a time period in a range of 1 to 60 min; and
rinsing off the keratin fibers and optionally shampooing the keratin fibers.

10. A method for permanently shaping keratin fibers, comprising:
optionally shampooing the keratin fibers;
putting the keratin fibers under mechanical tension;
applying to the keratin fibers an aqueous permanent waving composition E having a pH in a range of 3 to 12 comprising one or more reducing agents and one or more alkalizing agents, and leaving it for a time period in a range of 1 min to 60 min;
optionally rinsing off the aqueous permanent waving composition E;
applying the composition of claim 1 to the keratin fibers and leaving it for a time period in a range of 1 min to 30 min;
releasing the mechanical tension from the keratin fibers; and
rinsing off the keratin fibers and optionally shampooing the keratin fibers,
wherein the putting the keratin fibers under mechanical tension, the applying to the keratin fibers the aqueous permanent waving composition E, the releasing the mechanical tension and the rising off the keratin fibers may be performed in any order.

11. A method of improving a storage stability of aqueous compositions comprising hydrogen peroxide and having a pH in a range of 1 to 6, the method comprising adding one or more compounds selected from the one or more orthodiphenols and the one or more imidazolidine-2,4-diones of claim 1.

12. The composition according to claim 1, wherein the orthodiphenol is tiron or a salt thereof.

13. The composition according to claim 1, wherein the imidazolidin-2,4-dione is hydantoin or a salt thereof.

14. The composition according to claim 1, wherein a total concentration of the one or more compounds is in a range of 0.03% to 0.15% by weight, calculated to the total weight of the composition.

15. The composition according to claim 7, wherein the one or more surfactants are selected from non-ionic surfactants, anionic surfactants, cationic surfactants, amphoteric/zwitterionic surfactants, and salts thereof.

16. The kit-of-parts according to claim 8, wherein at least one of the orthodiphenols is selected from:

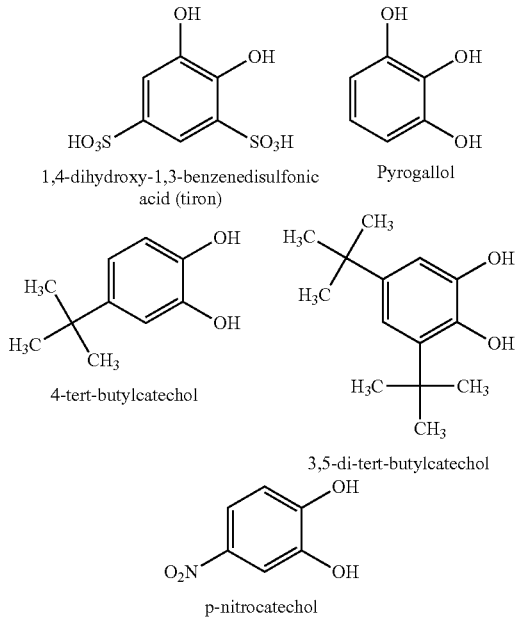

and salts thereof.

17. The kit-of-parts according to claim 8, wherein at least one of the imidazolidin-2,4-diones is hydantoin, allantoin or a salt thereof.

18. The method according to claim 10, wherein at least one of the orthodiphenols is selected from:

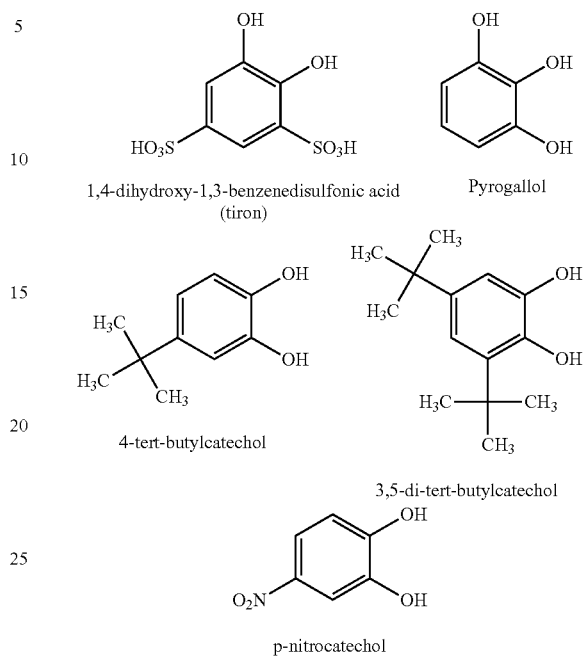

and salts thereof.

19. The method according to claim 10, wherein at least one of the imidazolidin-2,4-diones is hydantoin, allantoin or a salt thereof.

\* \* \* \* \*